United States Patent [19]

Kirchlechner

[11] 4,229,582
[45] Oct. 21, 1980

[54] PROCESS FOR THE PREPARATION OF STERICALLY UNIFORM, NATURAL 6-THIATETRACYCLINE DERIVATIVES

[75] Inventor: Richard Kirchlechner, Hähnlein, Fed. Rep. of Germany

[73] Assignee: Merck Patent Gesellschaft mit beschränkter Haftung, Darmstadt, Fed. Rep. of Germany

[21] Appl. No.: 951,207

[22] Filed: Oct. 13, 1978

[30] Foreign Application Priority Data

Oct. 13, 1977 [DE] Fed. Rep. of Germany ....... 2746044

[51] Int. Cl.³ .......................................... C07D 335/04
[52] U.S. Cl. ........................................ 549/25; 549/23
[58] Field of Search .......................... 260/328; 549/25

[56] References Cited

U.S. PATENT DOCUMENTS

| 3,988,468 | 10/1976 | Rogalski et al. | 260/328 X |
| 4,024,272 | 5/1977 | Rogalski et al. | 260/328 X |

*Primary Examiner*—John D. Randolph
*Attorney, Agent, or Firm*—Millen & White

[57] ABSTRACT

A process for the preparation of racemic 6-thiatetracycline derivatives comprises treating a mixture of epimers of corresponding 1,4,4a,5,5a,6,11,12a-octahydro-3,12-dihydroxy-1,11-dioxo-6-thianaphthacene-2-carboxamides with a saturated heterocyclic secondary amine having a total of 4 to 12 carbon atoms for a sufficient length of time at temperatures of about 15°–120° C.

8 Claims, No Drawings

PROCESS FOR THE PREPARATION OF STERICALLY UNIFORM, NATURAL 6-THIATETRACYCLINE DERIVATIVES

BACKGROUND OF THE INVENTION

The present invention relates to a novel process for the preparation of racemates consisting of 6-thiatetracycline derivates of "natural" configuration and their optical antipodes.

Hereinafter, the term "6-thiatetracycline" is used to refer to a racemate which consists of 4-dimethylamino-1,4,4a,5,5a,6-11,12a-octahydro-3,10,12,12a-tetrahydroxy-1,11-dioxo-6-thia-naphthacene-2-carboxamide having the configuration indicated in the formula.

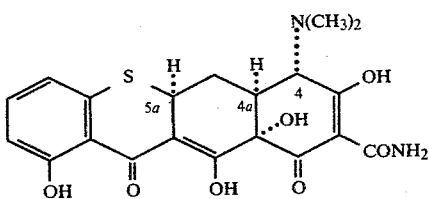

and its optical antipode.

A configuration in which the $C_{(4)}$ amino group and the two hydrogen atoms on $C_{(4a)}$ and $C_{(5a)}$ are in the syn-position relative to one another (as in 6-thiatetracycline) is termed "natural" herein, since it encompasses that of the naturally occurring tetracyclines produced by micro-organisms.

6-Thiatetracycline derivatives are known, for example from German Offenlegungsschrift No. 2,437,487 (U.S. Pat. No. 3,988,468) and German Offenlegungsschrift No. 2,442,829 (U.S. Pat. No. 4,024,272). In the syntheses described in these specifications, the tetracyclic system (octahydro-6-thianaphthacene) can be formed by a condensation reaction of 2-phenyl-4-[2-(5-hydroxy-thiochroman-4-on-2-yl)-ethylidene]-2-thiazolin-5-one (or oxazolin-5-one) with acetonedicarboxylic acid monomethyl ester monoamide. A mixture of the 4 possible racemates of 1,4,4a,5,5a,6,11,12a-octahydro-3,12-dihydroxy-1,11-dioxo-6-thianaphthacene-2-carboxamides, I to IV, is thus obtained which are shown schematically below:

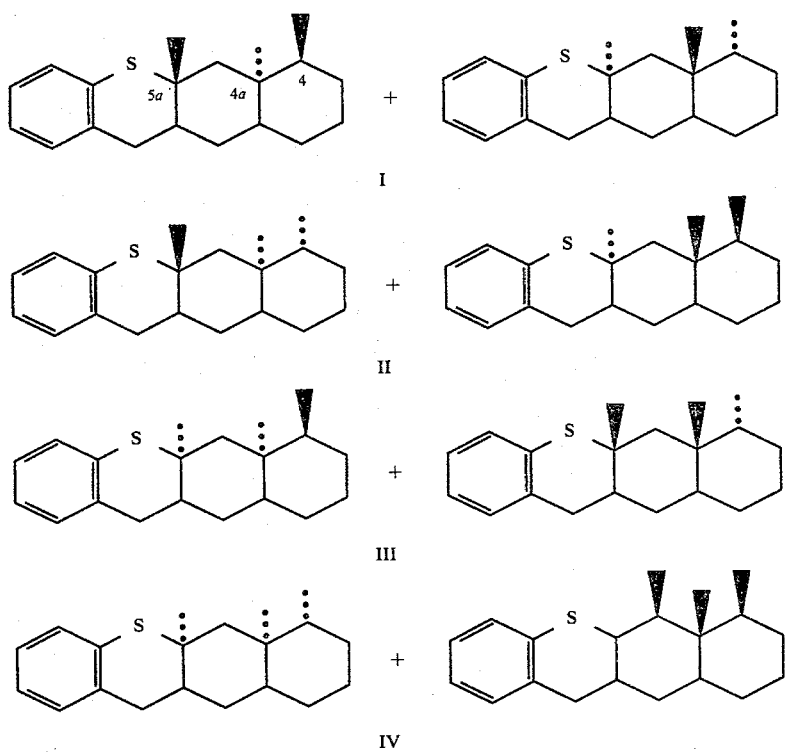

IV corresponds to the "natural" configuration. Compounds having this configuration display the greatest antibacterial activity and are therefore preferred. Efforts will therefore be made to convert the isomers I, II, and III, which belong to the less active series, into the isomer IV, the "4α, 4aα, 5aα"-antipode of which belongs to the most active series.

Thus, it is possible (see the above referenced U.S. patents) to epimerize the substituent in the 4-position in the desired manner, for example, by permitting it to stand in pyridine or piperidine. In this way, I can be converted into II and III can be converted into IV. Thus, using the crude product from the described condensation reaction as the starting material, a mixture can be obtained which consists only of II and IV.

These prior art processes, for example, epimerize by treating the stereoisomeric derivative with piperidine at 20° C. for 3½ hours (U.S. Pat. No. 3,988,468, column 7, lines 45–48) or with pyridine at 20° C. for 3 days (U.S. Pat. No. 4,024,272, column 11, lines 48–50).

However, hitherto, no route was known for converting the less desired II into the valuable IV. Therefore, in general, the resulting mixture had to be separated into its two components. This is a troublesome procedure because of the chemical similarity of the two components. For example, it was achievable using chromatographic methods. Moreover, in general, the isomer II had to be discarded since it could not be converted into secondary products which were pharmacologically active in vivo.

SUMMARY OF THE INVENTION

Accordingly, it is an object of the present invention to provide a process for converting a mixture of epimers containing at least two of the racemates I to IV into pure racemate IV.

It has now been found that, contrary to expectations, it is possible to convert II to IV, by treating II with a base, at elevated temperature and/or with a relatively long reaction time.

DETAILED DISCUSSION

Suitable bases include, in particular, saturated heterocyclic secondary amines having a total of 4–12, preferably 4–9, carbon atoms, especially piperidine and also, for example, pyrrolidine or morpholine.

Such bases include those having one or two non-aromatic rings, 4 to 7 ring atoms and one or two hetero ring atoms selected from O, N and S, preferably one N atom and zero or one O or S atom(s).

The reaction can be carried out in the presence or absence of an additional inert solvent. Suitable solvents include, for example, amides, preferably dimethylformamide (DMF), and also diethylformamide, dimethylacetamide and phosphoric acid hexamethyltriamide; and sulfoxides such as dimethylsulfoxide.

The reaction is appropriately carried out at temperatures of about 15°–120° C., e.g., 20°–70° C., and preferably 40°–60° C., such as 45°–60° C. The conversion is complete after about one hour at a reaction temperature of about 50°, after about 12 hours at 20°, after about 20 hours at 15° C., after about 10 to 20 minutes at 70° C., and after about 1 to 5 minutes at 120° C. Suitable reaction times at other temperatures can correspondingly be determined by routine chemical experimentation.

Generally, the minimum reaction time required for production of essentially pure IV by the epimerization of this invention will be geometrically related to the times given above for the specific temperatures mentioned, e.g., based on the values for 20° C. and 50° C. This kind of time/temperature relation is well-known to a skilled chemist who can easily estimate suitable reaction times at other temperatures by extrapolation from the values given above.

The reaction proceeds with high yields, virtually quantitatively, so that working up of the reaction mixture is greatly simplified, since only one isomer is present and, of the four possible isomers, this is the desired product only.

Since the amine normally is used as a solvent too, a great excess of it is preferably applied.

In particular, from 10–100 moles of base per mole of the mixture of epimers of IV can be used. When a solvent is employed, the concentration of the mixture of epimers is preferably about 2–20 weight percent, based on the total weight of solvent and epimer mixture. It is preferred that the epimerization be conducted under an inert gas atmosphere such as nitrogen, argon, etc.

The rates and order of addition of the materials used in the reaction are not critical.

By "pure" and "sterically uniform" is meant that the reaction product obtained contains essentially 100% of IV, e.g. 97–100% of IV.

Since an epimerization of the substituent in the 4-position is also effected by the action of the base, the crude product of the cyclization, which contains all four isomers, can be employed directly in the rearrangement reaction. In this reaction, the abovementioned epimerizations of I to II and of III to IV and the rearrangement of II to IV proceed in a "one-pot process". Thus, according to the process of this invention, not only II and II-containing mixtures, but quite conveniently, mixtures of epimers corresponding to IV, and especially mixtures of 5a-epimers corresponding to IV, can be converted to IV.

The subject of the invention is, accordingly, a process for the preparation of 6-thiatetracycline derivatives, characterized in that mixtures of epimers of 1,4,4a,5-,5a,6,11,12a-octahydro-3,12-dihydroxy-1,11-dioxo-6-thia-naphthacene-2-carboxamides are converted into sterically uniform 6-thiatetracycline derivatives having the natural configuration, by treatment with a base in accordance with the foregoing discussion.

Without intending to limit the invention in any way, it is theorized that the conversion of the ring system of rigid structure can be explained only by an intermediate opening of the ring.

Under the reaction conditions, the C ring of II opens in a retro-Michael reaction to give the intermediate product V—which is not isolated—and then closes again in a Michael reaction to give IV, which apparently is the thermodynamically more stable product:

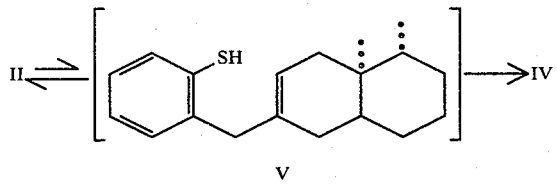

V

Even though the equilibrium between II and V may lie strongly on the side of II, it is still possible to convert virtually all the II epimers to IV.

In a preferred application, racemates consisting of 12α-dehydroxy-6-thiatetracyclines of formula VII and their optical antipodes are prepared by the process of this invention:

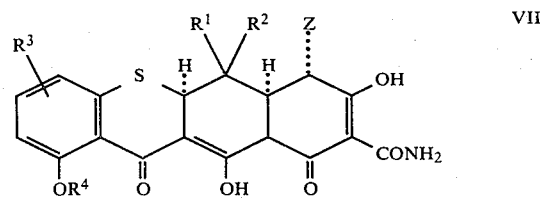

wherein $R^1$, $R^2$ and $R^4$ each is H or alkyl; $R^3$ is H, F, Cl, Br, $CF_3$, OH, alkyl, alkoxy, $NO_2$, $NH_2$, alkylamino, dialkylamino or acylamino; Z is a functionally modified amino group; and alkyl and alkoxy each is of 1–3 carbon atoms and acyl is of 1–4 carbon atoms.

In the compounds of Formula VII, the 4-amino group is preferably modified in the form of an acyl or thioacyl derivative or of an imino-ether or imino-thioether derived therefrom. Accordingly, it is preferably in the form of one of the groups $-NR^5-CY-R^6$ or $-N=C(YR^7)-R^6$, wherein $R^5$ is H or alkyl; $R^6$ is in particular (a) H, (b) alkyl having 1–10 carbon atoms or (c) a phenyl, benzyl, phenoxymethyl or phenoxypropyl radical each of which is unsubstituted, or monosubstituted or disubstituted by alkyl having 1–4 carbon atoms, OH, temporarily protected OH, CH$_2$OH containing an optionally temporarily protected OH group, NO$_2$, NH$_2$, alkylamino, dialkylamino, hydroxyalkylamino, acylamino, halogen, COOH, COO-alkyl, CONH$_2$ and/or CONH-alkyl; Y is an oxygen atom or a sulfur atom; and R$^7$ is alkyl, the alkyl groups preferably containing up to 4 carbon atoms and the acyl groups preferably containing up to 7 carbon atoms. Z is preferably a C$_6$H$_5$—CY—NH group.

The compounds obtainable according to the invention can be used as medicaments in human medicine and veterinary medicine or as intermediate products for the preparation of other medicaments. Thus, the process products, especially those of the formula VII, can be converted by known methods (see, for example, U.S. Pat. No. 4,024,272 whose disclosure is incorporated by reference herein) into other pharmacologically active 6-thiatetracycline derivatives. Thus, for example, 6-thiatetracycline itself is obtainable in a particularly convenient manner and in good total yield using the process of this invention. The products of the process of this invention are needed in medicine for treatments, e.g., of mammals, including humans, in accordance with U.S. Pat. No. 4,024,272.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

10.9 g of 2-phenyl-4-[2-(5-hydroxy-thiochroman-4-on-2-yl)-ethylidene]-2-thiazolin-5-one (m.p. 144°) and 5.8 g. of acetonedicarboxylic acid monomethyl ester monoamide are dissolved in 100 ml of dioxane, under nitrogen; 0.87 g. of sodium hydride (80% pure) is added and the mixture is stirred for one hour at 20°. An additional 2.6 g of sodium hydride are then added. The mixture is stirred for 10 minutes; 100 ml. of DMF are added; and the mixture is boiled for one hour. The mixture is cooled; excess sodium hydride is decomposed with methanol; and the mixture is poured into a mixture of ice and hydrochloric acid, with stirring. The mixture ("G") of stereoisomeric 4-thiobenzamido-1,4,4a,5,5a,6,11,12a-octahydro-3,10,12-trihydroxy-1,11-dioxo-6-thianaphthacene-2-carboxamides which has precipitated is filtered off, washed with water, dried and dissolved under nitrogen in a mixture of 75 ml of piperidine and 75 ml of DMF. The solution is warmed at 50° for one hour, cooled and stirred into a mixture of hydrochloric acid and ice. The resulting pure 4-dedimethylamino-4-thiobenzamido-12a-de-hydroxy-6-thiatetracycline ("D") is filtered off, washed with water, dried and recrystallized from acetone. M.P. 195°–196°.

The starting material is obtainable as follows:

5-Hydroxy-8-chloro-thiochroman-4-one-2-acetonitrile (compare German Offenlegungsschrift No. 2,442,829; U.S. Pat. No. 4,024,272) is hydrolyzed to the acid (m.p. 141°–143°); hydrogenolysis gives 5-hydroxy-thiochroman-4-one-2-acetic acid (m.p. 160°–164°), which is reduced via the resinous chloride by the Rosenmund method to the aldehyde (m.p. 69°). The latter is subjected to a condensation reaction with 2-phenyl-2-thiazolin-5-one.

EXAMPLE 2

21.2 g of 2-phenyl-4-[2-(5-hydroxy-8-dimethylamino-thiochroman-4-on-2-yl)-ethylidene]-2-thiazoline-5-one [m.p. 148°–150°; obtainable by ether cleavage of 5-methoxy-8-nitrothiochroman-4-one-2-acetic acid (compare German Offenlegungsschrift No. 2,442,829; U.S. Pat. No. 4,024,272) to 5-hydroxy-8-nitrothiochroman-4-one-2-acetic acid (m.p. 182°), reduction and subsequent methylation to 5-hydroxy-8-dimethylamino-thiochroman-2-acetic acid (m.p. 150°–152°), conversion to the chloride, reduction to the aldehyde (oily) and condensation reaction of the latter with 2-phenyl-2-thiazolin-5-one] and 8.75 g of acetonedicarboxylic acid monomethyl ester monoamide are dissolved in 200 ml of pyridine, under nitrogen. 0.5 g of NaH is added and the mixture is stirred overnight at 20°. An additional 4.9 g of NaH are then added; the mixture is boiled for 1.5 hours and cooled and is stirred into a mixture of ice and hydrochloric acid. Sodium hydroxide solution is added until the pH is 3–4. The mixture of stereoisomeric 4-thiobenzamido-7-dimethylamino-1,4,4a,5,5a,6,11,12a-octahydro-3,10,12-trihydroxy-1,11-dioxo-6-thianaphthacene-2-carboxamides which has precipitated is filtered off, washed with water, dried and dissolved in a mixture of 125 ml of piperidine and 125 ml of DMF. The solution is warmed at 50° for 75 minutes, and cooled and stirred into a mixture of hydrochloric acid and ice. After adding sodium hydroxide solution until the pH is 3–4, the resulting pure 4-dedimethylamino-4-thiobenzamido-7-dimethylamino-12a-de-hydroxy-6-thiatetracycline is filterd off, washed with water, dried and recrystallized from methylene chloride. M.p. 222°–223°.

The following compounds are obtained analogously:
4-dedimethylamino-4-thiobenzamido-7-methoxy-12a-dehydroxy-6-thiatetracycline, m.p. 253°–254°;
4-dedimethylamino-4-thiobenzamido-7-methoxy-12a-dehydroxy-6-thiatetracycline, m.p. 255°; and
4-dedimethylamino-4-thiobenzamido-8-methoxy-12a-dehydroxy-6-thiatetracycline, m.p. 212°–215°.

EXAMPLE 3

1 g of mixture "G" (compare Example 1) is dissolved in 5 ml of piperidine and the solution is left to stand overnight at 20°. After working up analogously to Example 1, pure "D" is obtained; m.p. 195°–196°.

EXAMPLE 4

1 g of mixture "G" is dissolved in 5 ml of morpholine, the solution is warmed at 50° for 1 hour and worked up analogously to Example 1 and pure "D" is obtained; m.p. 195°–196°.

EXAMPLE 5

1 g of "G" is dissolved in 10 ml of pyrrolidine, the solution is heated at 70° for 10 minutes, cooled and worked up analogously to Example 1 and pure "D" is obtained; m.p. 195°–196°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of racemic sterically uniform 6-thiatetracycline derivatives of "natural" configuration which comprises treating a mixture of epimers of corresponding 1,4,4a,5,5a,6,11,12a-octahydro-3,12-dihydroxy-1,11-dioxo-6-thia-naphthacene-2-carboxamides with a saturated heterocyclic amine having a total of 4 to 12 carbon atoms and one ring N atom at a temperature of about 15°–120° C. for a length of time effective to produce said racemic sterically uniform derivatives of "natural" configuration.

2. The process of claim 1 wherein the time/temperature relation is about 12 hours at 20° C. and about 1 hour at 50° C.

3. The process of claim 1 wherein the epimerization is conducted at a temperature of 20°–70° C.

4. The process of claim 1 wherein the base is piperidine, morpholine or pyrrolidine.

5. The process of claim 4 wherein the base is piperidine.

6. The process of claim 5 wherein the epimerization is conducted at a temperature of 50°–70° C. for 75 minutes - 10 minutes.

7. The process of claim 1 wherein the epimerization is conducted under a nitrogen atmosphere.

8. The process of claim 1 wherein the 6-thiatetracycline derivative is a racemate consisting of compounds of the formula

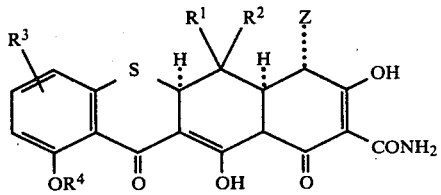

wherein $R^1$, $R^2$ and $R^4$ each is H or alkyl; $R^3$ is H, F, Cl, Br, $CF_3$, OH, alkyl, alkoxy, $NO_2$, $NH_2$, alkylamino, dialkylamino or acylamino; Z is a functionally modified amino group; and alkyl and alkoxy each is of 1–3 carbon atoms and acyl is of 1–4 carbon atoms, and the optical antipodes thereof.

* * * * *